US007482302B2

(12) United States Patent
Adachi et al.

(10) Patent No.: US 7,482,302 B2
(45) Date of Patent: Jan. 27, 2009

(54) FLUOROSULFONIC ACID COMPOUND, PROCESS FOR PRODUCING THE SAME, AND USE THEREOF

(75) Inventors: Kenji Adachi, Tsukuba (JP); Sumi Ishihara, Tsukuba (JP); Yoshichika Kuroki, Tsukuba (JP); Tsuyoshi Itagaki, Tsukuba (JP)

(73) Assignee: Daikin Industries, Ltd., Osaka-shi (JP)

( * ) Notice: Subject to any disclaimer, the term of this patent is extended or adjusted under 35 U.S.C. 154(b) by 42 days.

(21) Appl. No.: 10/545,387

(22) PCT Filed: Feb. 13, 2004

(86) PCT No.: PCT/JP2004/001547

§ 371 (c)(1),
(2), (4) Date: Jun. 19, 2006

(87) PCT Pub. No.: WO2004/072021

PCT Pub. Date: Aug. 26, 2004

(65) Prior Publication Data

US 2006/0252961 A1 Nov. 9, 2006

(30) Foreign Application Priority Data

Feb. 14, 2003 (JP) .............................. 2003-037417

(51) Int. Cl.
*B01J 31/00* (2006.01)
(52) U.S. Cl. ..................................... 502/168
(58) Field of Classification Search ................. None
See application file for complete search history.

(56) References Cited

U.S. PATENT DOCUMENTS 4,329,435 A 5/1982 Kimoto et al.

FOREIGN PATENT DOCUMENTS

| JP | 2002-3466 | 1/2002 |
| WO | WO 99/07676 A1 | 2/1999 |
| WO | WO 00/42028 A1 | 7/2000 |

OTHER PUBLICATIONS

Smith et al, "March's Advanced Organic Chemistry", Wiley, 6th edition, p. 1472.*
Takahashi et al., caplus an: 1973:147341.*
Sanchez et al., caplus an: 2007:1248830.*
Sartori et al. (1999), caplus AN 1999:113928.*
*Kagaku Binran* (Handbook of Chemistry), edited by the Chemical Society of Japan, basic vol., 4th edition, II-347, II-348. (Discussed in the Specification) 1964.
Kotoris, Christopher C., et al.; "Preparation of Benzylic α, α-Difluoronitriles, -tetrazoles, and -sulfonates via Electrophilic Fluorination;" *J. Org. Chem.*; vol. 63, pp. 8052-8057 (1998). (Discussed in the Specification).

Chen, Mei-Jin, et al.; "Synthesis of Estrone-3-Sulfate Analogues Bearing Novel Non-Hydrolyzable Sulfate Mimetics;"*Tetrahedron Letters*; vol. 40, pp. 4149-4152 (1999). (Discussed in the Specification).
Gandel'sman, L. Z., et al.; "Acylation of Aromatic Compounds in the Presence of Sulfodifluoroacetic Acid;" *Ukrainskii Khimicheskii Zhurnal*, vol. 52, No. 4, pp. 405-406 (1986). (copies attached are the published translation, *Soviet Progress in Chemistry*; pp. 75,76, and index pages). (Discussed in the Specification).
Sokol'Skii, G. A., et al.; "Fluorine-Containing β-Sultones, Communication 28. Reactions of β-Sultones With Ethylene Oxide;" *Izvestiya Akademii Nauk SSSR, Seriya Khimicheskaya*, No. 7, pp. 1565-1570 (1968). (copies attached are the published translation, *Bulletin of the Academy of Sciences of the USSR*; pp. 1470-1474, and index pages). (Discussed in the Specification).
Agafonov, I. L., et al.; "Mass Spectrum of Tetrabutyltin;" *Izvestiya Akademii Nauk SSSR, Seriya Khmicheskaya*, No. 6, pp. 1289-1293 (1968). (copies attached are the published translation, *Bulletin of the Academy of Sciences of the USSR*; pp. 1216-1220, and index pages). (Discussed in the Specification).
Bekker, R. A., et al.; "Polyfluorinated Enols and Their Derivatives, III. Halogenation, Sulfonation, and Nitrosation of Perfluoropropen-2-ol;"*Zhurnal Organicheskoi Khimii*, vol. 11, No. 8, pp. 1604-1607 (1975). (copies attached are the published translation, *Journal of Organic Chemistry of the USSR*; pp. 1588-1591, and index pages). (Discussed in the Specification).
O'Sullivan, E. J. M., et al.; "Application of Electrochemical Fluorination to the Synthesis of Perfluoroalkane Sulfonic Acid Electrolytes;" *J. Electrochem. Soc.*; vol. 132, No. 10, pp. 2424-2426 (1985). (Discussed in the Specification).
Jüschke, R., et al.; "Synthesis of Novel Lithium Salts with Doubly Charged Anions for Secondary Batteries;" *Z. Naturforsch*, vol. 53, No. 2, pp. 135-144 (1998). (Discussed in the Specification).

(Continued)

*Primary Examiner*—Kamal A Saeed
*Assistant Examiner*—Sun Jae Y Loewe
(74) *Attorney, Agent, or Firm*—Kratz, Quintos & Hanson, LLP

(57) ABSTRACT

The present invention provides novel fluorosulfonic acids and salts thereof having greater stability and higher acidity than conventional fluorosulfonic acids; and synthetic intermediates thereof. The invention also provides processes for producing novel fluorosulfonic acids from which various derivatives can be easily synthesized; and uses of these fluorosulfonic acids. Specifically, the invention provides a compound represented by formula (1):

$$R-S(=O)_n-CF_2-SO_3H \qquad (1)$$

wherein R is a group bound to an adjacent sulfur atom through a carbon atom, examples of R being an optionally substituted alkyl group, an optionally substituted haloalkyl group, an optionally substituted alkenyl group, an optionally substituted haloalkenyl group, an optionally substituted alkynyl group, an optionally substituted haloalkynyl group, an optionally substituted cycloalkyl group, etc.; and n is 1 or 2. The invention also provides salts of such a compound, etc.

6 Claims, No Drawings

OTHER PUBLICATIONS

Gard, G. L., et al.; "(Pentafluoro-$\lambda^6$-sulfanyl) difluoromethanesulfonyl Fluoride and Derivatives;" *Inorg. Chem.*, vol. 29, No. 22, pp. 4588-4590 (1990). (Discussed in the Specification).

Waterfeld, A., et al.; "A new cyclic fluorinated trisulfone $(CF_2SO_2)_3$ and fluorinated derivatives: $SO_2(CF_2SO_2F)_2$, $CF_2(SO_2CF_3)_2$, $CF_3SO_2CF_2SO_2F$, $CF_2(SO_2F)_2$ and $CF_3SO_2CF_2SO_2CF_2SO_2F$;" *Journal of Fluorine Chemistry*, vol. 67, pp. 27-31 (1994). (Discussed in the Specification).

Mizerski, A., et al.; "Transformations of 4-chlorophenyl-difluoromethyl sulfone into new compounds with potential pesticidal activity", *Pestycydy*, (1-2), pp. 29-41 (2001). (Discussed in the Specification).

Stahly, Patrick G.; "Nucleophilic Addition of Difluoromethyl Phenyl Sulfone to Aldehydes and Various Transformations of the Resulting Alcohols;" *Journal of Fluorine Chemistry*; vol. 43, pp. 53-66 (1989). (Discussed in the Specification).

Moore, George G. I.; "Fluoroalkanesulfonyl Chlorides;" *J. Org. Chem.* vol. 44, No. 10, pp. 1708-1711 (1979). (Discussed in the Specification).

Tordeux, M., et al.; "Reactions of Bromotrifluoromethane and Related Halides Part VII [1] Condensations With Thiocyanates and Isocyanates in the Presence of Zinc;" J.Fluorine. Chem., vol. 43, pp. 27-34 (1989). (Discussed in the Specification).

Doyle, M., et al.; "High-Temperature Proton Conducting Membranes Based on Perfluorinated Ionomer Membrane-Ionic Liquid Composites;" *Journal of The Electrochemical Society*, vol. 147, No. 1, pp. 34-37 (2000). (Discussed in the Specification).

International Search Report for corresponding PCT international application, PCT/JP2004/001547, dated May 18, 2004. (Discussed in the Specification).

* cited by examiner

FLUOROSULFONIC ACID COMPOUND, PROCESS FOR PRODUCING THE SAME, AND USE THEREOF

TECHNICAL FIELD

The present invention relates to novel fluorosulfonic acids and synthetic intermediates thereof. The invention also relates to processes for producing these fluorosulfonic acids and uses thereof.

BACKGROUND ART

Generally, organic sulfonic acid compounds are used for acid catalysts, ion exchange membranes, etc., in synthetic reactions because of their high acidity, and the salts of organic sulfonic acid compounds have a wide range of uses such as cell electrolytes, photo acid generators in resist materials, photosensitized solar cells, capacitors, solvents, etc. In particular, sulfonic acid compounds wherein the carbon in the α-position to a sulfonic acid group is substituted with fluorine have extremely high acidity and exhibit interesting characteristics.

For example, fluorosulfonic acids represented by formula (A):

$$R^0\text{—}CF_2\text{—}SO_3H \tag{A}$$

are used as acid catalysts, etc., because of their high acidity, and salts thereof are used as cell electrolytes, etc. Specifically, such compounds that have been reported include:

compounds wherein $R^0$ is a fluorine atom or a fluoroalkyl group; compounds wherein $R^0$ is an aryl group (see J. Org. Chem., 1998, 63, 8052-8057 and Tetrahedron Letters, 1999, 40, 4149-4152); compounds wherein $R^0$ is a cyano group (see Japanese Unexamined Patent Publication No. 2002-3466); compounds wherein $R^0$ is a carboxyl group, an ester group, or a carbamoyl group (see Ukr. Khim. Zh. (Russ. Ed.), 1986, 52(4), 405-6; Izv. Akad. Nauk SSSR, Ser. Khim., 1968, 7, 1565-70; and Izv. Akad. Nauk SSSR, Ser. Khim., 1967, 6, 1289-94); compounds wherein $R^0$ is an acyl group (see Zh. Org. Khim., 1975, 11(8), 1604-7); compounds wherein $R^0$ is a sulfonic acid group, a salt thereof, or a sulfonamide group (see J. Electrochem. Society, 1985, 132(10), 2424-6 and Z. Naturforsch., B: Chemical Sci., 1998, 53(2), 135-144); compounds wherein $R^0$ is —$SF_5$ (see Inorg. Chem., 1990, 29(22), 4588-90); etc. These fluorosulfonic acids are organic acids having high acidity.

The application of high-acidity fluorosulfonic acids and derivatives thereof is expected not only in the above-mentioned uses but in a wide range of fields in which the characteristic properties thereof can be put to use. Therefore, a stable organic fluorosulfonic acid is strongly desired that has even higher acidity than the above-mentioned known fluorosulfonic acids and that easily allows various derivatives to be synthesized therefrom.

In addition, J. Fluorine Chem., 1994, 67, 27-31 reports fluorosulfonyl fluorides such as $CF_3SO_2CF_2SO_2F$, $FSO_2CF_2SO_2CF_2SO_2F$, $CF_3SO_2CF_2SO_2CF_2SO_2F$, etc.

DISCLOSURE OF THE INVENTION

An object of the present invention is to provide novel fluorosulfonic acids having greater stability and higher acidity than conventional fluorosulfonic acids; and synthetic intermediates therefor.

Another object of the invention is to provide processes for producing these fluorosulfonic acids, from which various derivatives can be easily synthesized; and uses of these fluorosulfonic acids.

In order to achieve the above objects, the present inventors conducted extensive research. As a result, the inventors found that novel fluorosulfonic acids having greater stability and higher acidity than conventional fluorosulfonic acids can be produced. The inventors conducted further research and thereby accomplished the present invention.

The present invention relates to the following fluorosulfonic acids and salts thereof, and processes for producing these.

Item 1: A compound having a group represented by the following formula in a molecule:

$$\text{—}S(\!=\!O)_n\text{—}CF_2\text{—}SO_3H$$

wherein n is 1 or 2;
or a salt of such a compound.

Item 2: A compound represented by formula (1):

$$R\text{—}S(\!=\!O)_n\text{—}CF_2\text{—}SO_3H \tag{1}$$

wherein R is an optionally substituted alkyl group, an optionally substituted haloalkyl group, an optionally substituted alkenyl group, an optionally substituted haloalkenyl group, an optionally substituted alkynyl group, an optionally substituted haloalkynyl group, an optionally substituted cycloalkyl group, an optionally substituted cycloalkenyl group, an optionally substituted aryl group, an optionally substituted heterocyclic group, an optionally substituted alkoxycarbonyl group, an optionally substituted alkenyloxycarbonyl group, an optionally substituted alkynyloxycarbonyl group, an optionally substituted aryloxycarbonyl group, an optionally substituted acyl group, an optionally substituted carbamoyl group, or a cyano group; and n is 1 or 2;
or a salt of such a compound.

Item 3: A compound represented by formula (2):

$$R\text{—}S\text{—}CF_2\text{—}SO_3H \tag{2}$$

wherein each symbol is as defined above;
or a salt of such a compound.

Item 4: A compound represented by formula (3):

$$R\text{—}S(\!=\!O)_n\text{—}CF_2\text{—}SO_2X \tag{3}$$

wherein X is a halogen atom, and the other symbols are as defined above;
with the proviso that the compound is not $CF_3SO_2CF_2SO_2F$, $FSO_2CF_2SO_2CF_2SO_2F$, or $CF_3SO_2CF_2SO_2CF_2SO_2F$.

Item 5: A compound represented by formula (4):

$$R\text{—}S\text{—}CF_2\text{—}SO_2X \tag{4}$$

wherein each symbol is as defined above.

Item 6: A process for producing a compound represented by formula (8):

$$R\text{—}S\text{—}CH_2\text{—}SO_3H \tag{8}$$

wherein each symbol is as defined above,
or a salt of such a compound;
the process comprising reacting a compound represented by formula (6):

$$R\text{—}SM \tag{6}$$

wherein M is a hydrogen atom or a metal atom, and the other symbols are as defined above;

with a compound represented by formula (7):

$$Y\text{—}CH_2\text{—}SO_3M_0 \qquad (7)$$

wherein Y is a halogen atom, and $M_0$ is a metal atom;

and optionally forming a salt of the resulting product.

Item 7: A process for producing a compound represented by formula (2):

$$R\text{—}S\text{—}CF_2\text{—}SO_3H \qquad (2)$$

wherein each symbol is as defined above, or a salt of such a compound;

the process comprising fluorinating a compound represented by formula (8):

$$R\text{—}S\text{—}CH_2\text{—}SO_3H \qquad (8)$$

wherein each symbol is as defined above, or a salt of such a compound;

and optionally forming a salt of the resulting product.

Item 8: A process for producing a compound represented by formula (1):

$$R\text{—}S(\!\!=\!\!O)_n\text{—}CF_2\text{—}SO_3H \qquad (1)$$

wherein each symbol is as defined above, or a salt of such a compound;

the process comprising oxidizing a compound represented by formula (2):

$$R\text{—}S\text{—}CF_2\text{—}SO_3H \qquad (2)$$

wherein each symbol is as defined above, or a salt of such a compound;

and optionally forming a salt of the resulting product.

Item 9: A process for producing a compound represented by formula (3):

$$R\text{—}S(\!\!=\!\!O)_n\text{—}CF_2\text{—}SO_2X \qquad (3)$$

wherein each symbol is as defined above;

the process comprising oxidizing a compound represented by formula (12):

$$R\text{—}S(\!\!=\!\!O)_n\text{—}CF_2\text{—}SR^1 \qquad (12)$$

wherein $R^1$ is an optionally substituted alkyl group, an optionally substituted haloalkyl group, an optionally substituted cycloalkyl group, or an optionally substituted aryl group; and the other symbols are as defined above.

Item 10: A process for producing a compound represented by formula (1):

$$R\text{—}S(\!\!=\!\!O)_n\text{—}CF_2\text{—}SO_3H \qquad (1)$$

wherein each symbol is as defined above, or a salt of such a compound;

the process comprising hydrolyzing a compound represented by formula (3):

$$R\text{—}S(\!\!=\!\!O)_n\text{—}CF_2\text{—}SO_2X \qquad (3)$$

wherein each symbol is as defined above;

and optionally forming a salt of the resulting product.

Item 11: A compound represented by formula (12a):

$$R\text{—}S(\!\!=\!\!O)_n\text{—}CF_2\text{—}S\text{—}CH_2\text{—}Ph \qquad (12a)$$

wherein each symbol is as defined above.

Item 12: An electrolyte comprising the compound or salt thereof according to item 1 or 2.

Item 13: A cell comprising the electrolyte of item 12.

Item 14: An acid catalyst comprising the compound or salt thereof according to item 1 or 2.

DETAILED DESCRIPTION OF THE INVENTION

The present invention is described below in detail.

I. Compound (1) and Salt Thereof

The present invention provides a compound having a group represented by the following formula in a molecule:

$$\text{—}S(\!\!=\!\!O)_n\text{—}CF_2\text{—}SO_3H$$

wherein n is 1 or 2; or a salt of such a compound. Specifically, the present invention provides a compound represented by formula (1):

$$R\text{—}S(\!\!=\!\!O)_n\text{—}CF_2\text{—}SO_3H \qquad (1)$$

wherein each symbol is as defined above; or a salt of such a compound.

In compound (1) of the present invention, R is a group bound to an adjacent sulfur atom through a carbon atom.

Examples of the alkyl group in an optionally substituted alkyl group represented by R include linear and branched $C_1$ to $C_{20}$ alkyl groups such as methyl, ethyl, n-propyl, isopropyl, n-butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, etc. In particular, typical examples thereof are linear and branched $C_1$ to $C_6$ alkyl groups.

Examples of substituents in the above optionally substituted alkyl group include aryl, aryloxy, alkoxy, haloalkoxy, alkenyloxy, alkynyloxy, alkoxycarbonyl, alkenylcarbonyl, alkynylcarbonyl, acyl, carbamoyl, alkylthio, cyano, nitro, amino, monoalkylamino, dialkylamino, hydroxy, etc. The alkyl group may be substituted with 1 to 3 identical or different substituents selected from such examples.

In compound (1) of the present invention, the haloalkyl group in an optionally substituted haloalkyl group represented by R is a substituted alkyl group wherein at least one hydrogen atom in the above-mentioned alkyl group is substituted by halogen atom. Examples thereof include linear and branched $C_1$ to $C_{20}$ haloalkyl groups. In particular, examples thereof include linear and branched $C_1$ to $C_{20}$ fluoroalkyl groups, wherein the halogen atom is fluorine atom. Specific examples include linear and branched $C_1$ to $C_{20}$ perfluoroalkyl groups such as trifluoromethyl, perfluoropropyl, perfluoroisopropyl, perfluorobutyl, perfluorohexyl, perfluorooctyl, perfluorodecyl, etc.; and linear and branched $C_1$ to $C_{20}$ polyfluoroalkyl groups such as trifluoroethyl, trichloroethyl, tetrafluoroethyl, hexafluoroisopropyl, 2-(perfluorooctyl)ethyl, 1H,1H,3H-tetrafluoropropyl, 1H,1H,5H-octafluoropentyl, perfluoro-7-methyloctyl, 4H-octafluorobutyl, 6-bromohexyl, 5,6-dibromohexyl, 8-iodooctyl, 1H,1H,7H-dodecafluoroheptyl, 6-(perfluorobutyl)hexyl, 2-(perfluoro-5-methylhexyl)ethyl, 2-(perfluorooctyl)ethyl, 3-(perfluorooctyl)propyl, 3-(perfluoro-3-methylbutyl)ethyl, 1H,1H-2, 5-di (trifluoromethyl)-3,6-dioxaundecafluorononyl, etc. In particular, $C_1$ to $C_6$ perfluoroalkyl groups and $C_1$ to $C_6$ polyfluoroalkyl groups are preferable.

Examples of substituents in the above optionally substituted haloalkyl group include aryl, aryloxy, alkoxy, haloalkoxy, alkenyloxy, alkynyloxy, alkoxycarbonyl, alkenylcarbonyl, alkenyl, alkynylcarbonyl, acyl, carbamoyl, alkylthio, cyano, nitro, amino, monoalkylamino, dialkylamino, hydroxy, perfluoroalkenyl, perfluoroalkenyloxy, etc. The haloalkyl group may be substituted with 1 to 3 identical or different substituents selected from such examples.

Examples of the above perfluoroalkenyl groups include $C_2$ to $C_4$ perfluoroalkenyl groups represented by $F_2C=CF-$, $FC(CF_3)=CF-$, $F_2C=C(CF_3)-$, etc. Examples of the above perfluoroalkenyloxy groups include $C_2$ to $C_4$ perfluoroalkenyloxy groups represented by $F_2C=CF-O-$, $FC(CF_3)=CF-O-$, $F_2C=C(CF_3)-O-$, etc.

In compound (1) of the present invention, examples of the alkenyl group in an optionally substituted alkenyl group represented by R include linear and branched $C_2$ to $C_{20}$ alkenyl groups. Specific examples thereof include vinyl, crotyl, 1-propenyl, isopropenyl, allenyl, 2-butenyl, 1,3-butadienyl, 3-pentenyl, 4-pentenyl, isoprenyl, 4-hexenyl, 5-hexenyl, 3,5-hexadienyl, 7-octenyl, styryl, cinnamyl, 5,7,9-decatrienyl, 17-octadecenyl, 2-nonyl-2-butenyl, etc. The alkenyl groups may be oxidized like epoxides.

Examples of substituents in the above optionally substituted alkenyl group include aryl, aryloxy, alkoxy, haloalkoxy, alkenyloxy, alkynyloxy, alkoxycarbonyl, alkenylcarbonyl, alkynylcarbonyl, acyl, carbamoyl, alkylthio, cyano, nitro, amino, monoalkylamino, dialkylamino, hydroxy, etc. The alkenyl group may be substituted with 1 to 3 identical or different substituents selected from such examples.

In compound (1) of the present invention, the haloalkenyl group in an optionally substituted haloalkenyl group represented by R is a substituted alkenyl group wherein at least one hydrogen atom in the above-mentioned alkenyl group is substituted by halogen atom. Examples thereof include linear and branched $C_2$ to $C_{20}$ haloalkenyl groups. In particular, examples thereof include linear and branched $C_2$ to $C_{20}$ fluoroalkenyl groups, wherein the halogen atom is fluorine atom.

Examples of substituents in the above optionally substituted haloalkenyl group include aryl, aryloxy, alkoxy, haloalkoxy, alkenyloxy, alkynyloxy, alkoxycarbonyl, alkenylcarbonyl, alkynylcarbonyl, acyl, carbamoyl, alkylthio, cyano, nitro, amino, monoalkylamino, dialkylamino, hydroxy, etc. The haloalkenyl group may be substituted with 1 to 3 identical or different substituents selected from such examples.

In compound (1) of the present invention, examples of the alkynyl group in an optionally substituted alkynyl group represented by R include linear and branched $C_2$ to $C_{20}$ alkynyl groups. Specific examples thereof include ethynyl, 2-propynyl, 2-butynyl, 3-butynyl, 3-pentynyl, 4-pentynyl, 4-hexynyl, 5-hexynyl, 2-pentene-4-ynyl, 4-ethyl-5-heptynyl, 7-octynyl, 8-decynyl, 15-hexadecynyl, etc. In particular, examples thereof include $C_2$ to $C_{10}$ alkynyl groups. Such alkynyl groups may include double bonds.

Examples of substituents in the above optionally substituted alkynyl group include halogen atoms, aryl, aryloxy, alkoxy, haloalkoxy, alkenyloxy, alkynyloxy, alkoxycarbonyl, alkenylcarbonyl, alkynylcarbonyl, acyl, carbamoyl, alkylthio, cyano, nitro, amino, monoalkylamino, dialkylamino, hydroxy, etc. The alkynyl group may be substituted with 1 to 3 identical or different substituents selected from such examples.

In compound (1) of the present invention, the haloalkynyl group in an optionally substituted haloalkynyl group represented by R is a substituted alkynyl group wherein at least one hydrogen atom in the above-mentioned alkynyl group is substituted by halogen atom. Examples thereof include $C_2$ to $C_{10}$ haloalkynyl groups. Such alkynyl groups may include double bonds. The halogen atom is preferably fluorine.

Examples of substituents in the above optionally substituted haloalkynyl group are those mentioned as substituents in the optionally substituted alkynyl group. The haloalkynyl group may be substituted with identical or different substituent(s) selected from such examples.

In compound (1) of the present invention, examples of the cycloalkyl group in an optionally substituted cycloalkyl group represented by R include $C_3$ to $C_{20}$ cycloalkyl groups such as cyclopropyl, cyclobutyl, cyclopentyl, cyclohexyl, cycloheptyl, decahydronaphthalenyl, norbornyl, bicyclo[3.2.1]octyl, bicyclo[5.2.0]nonyl, spiro[3.4]octyl, spiro[4.5]decyl, spirobicyclohexyl, etc. In particular, examples thereof include $C_4$ to $C_6$ cycloalkyl groups such as cyclobutyl, cyclopentyl, cyclohexyl, etc.

Examples of substituents in the above optionally substituted cycloalkyl group include halogen atoms, alkyl, aryl, aryloxy, alkoxy, haloalkoxy, alkenyloxy, alkynyloxy, alkoxycarbonyl, alkenylcarbonyl, alkynylcarbonyl, acyl, carbamoyl, alkylthio, cyano, nitro, amino, monoalkylamino, dialkylamino, hydroxy, etc. The cycloalkyl group may be substituted with 1 to 3 identical or different substituents selected from such examples.

In compound (1) of the present invention, examples of the cycloalkenyl group in an optionally substituted cycloalkenyl group represented by R include $C_3$ to $C_{20}$ cycloalkenyl groups such as cyclobutenyl, cyclopentenyl, cyclopentadienyl, cyclohexenyl, 1,3-cyclohexadienyl, norbornenyl, menthenyl, bornenyl, indenyl, octahydronaphthalenyl, 2-cyclohexenespiro-2'-cyclopentenyl, etc. In particular, examples thereof include $C_4$ to $C_6$ cycloalkenyl groups.

Examples of substituents in the above optionally substituted cycloalkenyl group are those mentioned as substituents in the optionally substituted cycloalkyl group. The cycloalkenyl group may be substituted with 1 to 3 identical or different substituents selected from such examples.

In compound (1) of the present invention, examples of the aryl group in an optionally substituted aryl group represented by R include $C_6$ to $C_{20}$ monocyclic, bicyclic, tricyclic, or tetracyclic aryl groups such as phenyl, naphthyl, phenanthryl, anthryl, pyrenyl, etc. In particular, examples thereof include phenyl groups.

Examples of substituents in the above optionally substituted aryl group include halogen atoms, alkyl, alkenyl, aryl, aryloxy, alkoxy, haloalkoxy, alkenyloxy, alkynyloxy, alkoxycarbonyl, alkenylcarbonyl, alkynylcarbonyl, acyl, carbamoyl, alkylthio, cyano, nitro, amino, monoalkylamino, dialkylamino, hydroxy, etc. The aryl group may be substituted with 1 to 3 identical or different substituents selected from such examples.

Specific examples of substituted aryl groups include tolyl, chlorophenyl, fluorophenyl, dichlorophenyl, difluorophenyl, pentafluorophenyl, cyanophenyl, nitrophenyl, dinitrophenyl, methoxyphenyl, diphenyl, vinylphenyl, propenylphenyl, etc.

In compound (1) of the present invention, examples of the heterocyclic group in an optionally substituted heterocyclic group represented by R include aliphatic heterocyclic groups and aromatic heterocyclic groups.

Examples of aliphatic heterocyclic groups include $C_5$ to $C_{20}$ monocyclic, bicyclic, or tricyclic aliphatic heterocyclic groups having 1 to 4 identical or different hetero atoms selected from the group consisting of nitrogen, oxygen, sulfur, phosphorus, silicon, and boron. Such aliphatic heterocyclic groups may include double bonds. The hetero atoms may be oxidized. Specific examples of aliphatic heterocyclic groups include piperidyl, piperazinyl, pyrrolidinyl, tetrahydrofuryl, pyranyl, dioxolanyl, dioxanyl, tetrahydrothienyl, pentamethylene sulfidyl, dithianyl, thioxanyl, pyrrolidinyl, piperidinyl, morpholinyl, etc. In particular, examples thereof include $C_5$ to $C_8$ monocyclic aliphatic heterocyclic groups.

Examples of aromatic heterocyclic groups include $C_5$ to $C_{14}$ monocyclic, bicyclic, or tricyclic aromatic heterocyclic groups having 1 to 4 identical or different hetero atoms selected from the group consisting of nitrogen, oxygen, sulfur, phosphorus, silicon, and boron. Specific examples of aromatic heterocyclic groups include furyl, thienyl, imidazolyl, oxazolyl, thiazolyl, pyrrolyl, pyrrolidinyl, triazolyl, tetrazolyl, benzothiazolyl, benzoimidazolyl, oxadiazolyl, thiadiazolyl, indolyl, pyrazolyl, pyridazinyl, cinnolinyl, quinolyl, isoquinolyl, quinoxalinyl, pyrazinyl, pyridyl, benzofuryl, benzothienyl, tetrazolyl, isobenzofuranyl, chromenyl, thianthrenyl, isothiazolyl, phenoxazinyl, etc. In particular, examples thereof include $C_5$ to $C_8$ monocyclic aliphatic heterocyclic groups.

Examples of substituents in the above optionally substituted heterocyclic group include halogen atoms, alkyl, aryl, aryloxy, alkoxy, haloalkoxy, alkenyloxy, alkynyloxy, alkoxycarbonyl, alkenylcarbonyl, alkynylcarbonyl, acyl, carbamoyl, alkylthio, cyano, nitro, amino, monoalkylamino, dialkylamino, hydroxy, etc. The heterocyclic group may be substituted with 1 to 3 identical or different substituents selected from such examples.

In compound (1) of the present invention, examples of the alkoxycarbonyl group in an optionally substituted alkoxycarbonyl group represented by R include linear and branched $C_1$ to $C_{10}$ alkoxycarbonyl groups. Specific examples thereof include methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl, pentyloxycarbonyl, hexyloxycarbonyl, etc.

Examples of substituents in the above optionally substituted alkoxycarbonyl group include halogen atoms, aryl, aryloxy, alkoxy, haloalkoxy, alkenyloxy, alkynyloxy, alkoxycarbonyl, alkenylcarbonyl, alkynylcarbonyl, acyl, carbamoyl, alkylthio, cyano, nitro, amino, monoalkylamino, dialkylamino, hydroxy, etc. The alkoxycarbonyl group may be substituted with 1 to 3 identical or different substituents selected from such examples.

Specific examples of substituted alkoxycarbonyl groups include 2-phenylethyloxycarbonyl, benzyloxycarbonyl, 1-phenylethyloxycarbonyl, 3-phenylpropyloxycarbonyl, 4-phenylbutyloxycarbonyl, naphthyloxycarbonyl, etc.

In compound (1) of the present invention, examples of the alkenyloxycarbonyl group in an optionally substituted alkenyloxycarbonyl group represented by R include vinyloxycarbonyl, 2-propenyloxycarbonyl, 3-pentenyloxycarbonyl, 4-pentenyloxycarbonyl, 5-hexenyloxycarbonyl, 3,5-hexadienyloxycarbonyl, 7-octenyloxycarbonyl, etc.

Examples of substituents in the above optionally substituted alkenyloxycarbonyl group are those mentioned as substituents in the optionally substituted alkoxycarbonyl group. The alkenyloxycarbonyl group may be substituted with 1 to 3 identical or different substituents selected from such examples.

In compound (1) of the present invention, examples of the alkynyloxycarbonyl group in an optionally substituted alkynyloxycarbonyl group represented by R include ethynyloxycarbonyl, 2-propynyloxycarbonyl, 3-pentynyloxycarbonyl, 4-hexynyloxycarbonyl, 5-hexynyloxycarbonyl, 8-decynyloxycarbonyl, etc.

Examples of substituents in the above optionally substituted alkynyloxycarbonyl group are those mentioned as substituents in the optionally substituted alkoxycarbonyl group. The alkynyloxycarbonyl group may be substituted with one identical or different substituent selected from such examples.

In compound (1) of the present invention, examples of the aryloxycarbonyl group in an optionally substituted aryloxycarbonyl group represented by R include $C_1$ to $C_{14}$ monocyclic, bicyclic, or tricyclic aryloxycarbonyl groups. Specific examples thereof include phenoxycarbonyl, naphthyloxycarbonyl, phenanthryloxycarbonyl, anthryloxycarbonyl, etc.

Examples of substituents in the above optionally substituted aryloxycarbonyl group are those mentioned as substituents in the optionally substituted alkoxycarbonyl group. The aryloxycarbonyl group may be substituted with 1 to 3 identical or different substituents selected from such examples.

In compound (1) of the present invention, examples of the acyl group in an optionally substituted acyl group represented by R include linear and branched $C_1$ to $C_6$ alkanoyl groups such as formyl, acetyl, propionyl, n-butyryl, isobutyryl, valeryl, isovaleryl, pivaloyl; arylcarbonyl groups such as benzoyl, naphthoyl; etc.

Examples of substituents in the above optionally substituted acyl group include halogen atoms, alkyl, aryl, aryloxy, alkoxy, haloalkoxy, alkenyloxy, alkynyloxy, alkoxycarbonyl, alkenylcarbonyl, alkynylcarbonyl, acyl, carbamoyl, alkylthio, cyano, nitro, amino, monoalkylamino, dialkylamino, hydroxy, etc. The alkoxycarbonyl group may be substituted with 1 to 3 identical or different substituents selected from such examples.

Specific examples of substituted acyl groups include substituted acetyl groups such as chloroacetyl, bromoacetyl, dichloroacetyl, and trifluoroacetyl; alkoxy-substituted acetyl groups such as methoxyacetyl and ethoxyacetyl; alkylthio-substituted acetyl groups such as methylthioacetyl; substituted benzoyl groups such as phenoxyacetyl, phenylthioacetyl, 2-chlorobenzoyl, 3-chlorobenzoyl, 4-chlorobenzoyl, 4-methylbenzoyl, 4-t-butylbenzoyl, 4-methoxybenzoyl, 4-cyanobenzoyl, 4-nitrobenzoyl, and 4-vinylbenzoyl; etc.

In compound (1) of the present invention, examples of an optionally substituted carbamoyl group represented by R include those groups represented by the formula: —CONR$^a$R$^b$, wherein R$^a$ and R$^b$ each independently represent, for example, a hydrogen atom, or an alkyl, haloalkyl, aryl, haloaryl, aralkyl group, etc. Specific examples of substituted carbamoyl groups include N-methylcarbamoyl, N,N-dimethylcarbamoyl, N-phenylcarbamoyl, N-chlorophenylcarbamoyl, N,N-diethylcarbamoyl, etc.

Since compound (1) of the present invention has a sulfonic acid group, it can form salts. A salt of compound (1) of the present invention may be, for example, a metal salt, onium salt, etc.

The kind of metal atom that can form a metal salt of compound (1) of the invention is not restricted as long as it loses an electron and serves as a cation. Examples of such metal atoms include alkali metals such as lithium, sodium, potassium, cesium; alkaline earth metals such as beryllium, magnesium, calcium, barium; transition metals such as cerium, copper, nickel, silver, samarium, yttrium, europium, hafnium, lanthanum, scandium; other metals such as tin, mercury, zinc, indium, etc. Among these, alkali metals such as lithium, sodium and potassium are preferable.

Examples of onium salts of compound (1) of the present invention include nitrogen-containing onium salts, phosphonium salts, etc. A preferable example thereof is a nitrogen-containing onium salt.

Examples of nitrogen-containing onium salts include ammonium salts, ammonium salts having 1 to 4 substituents on the nitrogen atom, optionally substituted nitrogen-containing heterocyclic onium salts, phosphonium salts, etc.

Examples of substituents of ammonium salts having 1 to 4 substituents on the nitrogen atom include alkyl, aralkyl, aryl, cycloalkyl, haloalkyl, alkoxyalkyl, etc. In particular, typical examples are ammonium salts having 3 or 4 identical or different alkyl (preferably $C_1$ to $C_{10}$ alkyl) groups as substituents on the nitrogen atom.

The heterocycles that constitute optionally substituted nitrogen-containing heterocyclic onium salts may be nitrogen-containing aliphatic heterocycles or nitrogen-containing aromatic heterocycles. Examples of nitrogen-containing aliphatic heterocycles include piperidine, piperazine, aziridine, azetidine, pyrrolidine, 1-methylpyrrolidine, 3,5-dimethylpiperidine, 1,4-dimethylpiperazine, quinuclidine, 1,4-diazabicyclo[2,2,2]octane, morpholine, thiomorpholine, 4-methylmorpholine, etc. Examples of nitrogen-containing aromatic heterocycles include pyridine, pyrazine, pyrimidine, triazole, oxazole, pyrrole, 1-methylpyrrole, pyrazole, imidazole, 1-methylimidazole, tetrazole, isothiazole, thiazole, indole, carbazole, benzoxazole, purine, dipyridyl, pyridazine, triazine, quinoline, biquinoline, isoquinoline, acridine, quinozaline, quinazoline, phthalazine, phenanthridine, phenanthroline, etc. In particular, examples thereof include pyridine, imidazole, 1,2,4-triazole, etc.

Examples of substituents of nitrogen-containing heterocyclic onium salts include alkyl, haloalkyl, cycloalkyl, aralkyl, aryl, halogen atoms, alkoxy, aryloxy, aralkyloxy, alkoxycarbonyl, aryloxycarbonyl, acyl, nitro, cyano, amino, monoalkylamino, dialkylamino, hydroxy, etc. The nitrogen-containing heterocyclic onium salt may be substituted with 1 to 3 identical or different substituents selected from such examples.

Preferable examples of nitrogen-containing heterocyclic onium salts include trialkyl (especially tri($C_1$-$C_6$)alkyl) ammonium salts, pyridinium salts, imidazolium salts, 1,2,4-triazolium salts, etc.

Examples of phosphonium salts include those phosphonium salts having 3 or 4 substituents on the phosphorus atom. Examples of substituents of phosphonium salts include alkyl, aralkyl, aryl, cycloalkyl, haloalkyl, alkoxyalkyl groups, etc. The phosphorus atom of the phosphonium salt is substituted with 3 or 4 identical or different substituents selected from such examples.

Specific examples of compound (1) of the present invention include compounds represented by formula (1), wherein R is an optionally substituted alkyl group, an optionally substituted haloalkyl group, an optionally substituted alkenyl group, an optionally substituted haloalkenyl group, an optionally substituted cycloalkyl group, or an optionally substituted aryl group, and n is 1 or 2 (particularly 2); and alkali metal salts of such compounds, nitrogen-containing onium salts of such compounds, etc.

Examples of optionally substituted alkyl groups include $C_1$ to $C_{20}$ (preferably $C_1$ to $C_{10}$) alkyl groups optionally substituted with 1 or 2 identical or different groups selected from aryl and alkoxy groups.

Examples of optionally substituted haloalkyl groups include $C_1$ to $C_{20}$ (preferably $C_2$ to $C_{10}$) haloalkyl groups optionally substituted with 1 or 2 identical or different groups selected from aryl, alkoxy, haloalkenyloxy (preferably $C_2$ to $C_4$ perfluoroalkenyloxy and $C_2$ to $C_4$ polyfluoroalkenyloxy), and alkenyloxy (preferably $C_2$ to $C_4$ alkenyloxy) groups. In particular, examples thereof include $C_1$ to $C_{10}$ perfluoroalkyl and $C_1$ to $C_{10}$ polyfluoroalkyl groups.

Examples of optionally substituted alkenyl groups include $C_2$ to $C_{20}$ (preferably $C_2$ to $C_{10}$) alkenyl groups optionally substituted with 1 or 2 identical or different groups selected from aryl and alkoxy groups.

Examples of optionally substituted haloalkenyl groups include $C_2$ to $C_{20}$ (preferably $C_2$ to $C_{10}$, and more preferably $C_2$ to $C_6$) haloalkenyl groups optionally substituted with 1 or 2 identical or different groups selected from aryl and alkoxy groups. In particular, examples thereof include $C_2$ to $C_{10}$ (preferably $C_2$ to $C_6$) perfluoroalkenyl groups.

Examples of optionally substituted cycloalkyl groups include $C_3$ to $C_8$ (preferably $C_5$ to $C_7$) cycloalkyl groups optionally substituted with 1 or 2 identical or different groups selected from aryl and alkoxy groups.

Examples of optionally substituted aryl groups include aryl groups (especially phenyl groups) optionally substituted with 1 or 2 identical or different substituents selected from halogen atoms (I, Br, Cl and F; especially F), $C_1$ to $C_3$ alkoxy, alkenyl (preferably $C_2$ to $C_4$ alkenyl), haloalkenyl (preferably $C_2$ to $C_4$ perfluoroalkenyl), alkenyloxy (preferably $C_2$ to $C_4$ alkenyloxy), haloalkenyloxy (preferably $C_2$ to $C_4$ perfluoroalkenyloxy), and alkenylcarbonyl (wherein the alkenyl is preferably $C_2$ to $C_4$ perfluoroalkenyl) groups.

Examples of alkali metal atoms that form alkali metal salts include lithium, sodium, and potassium. A preferable example thereof is lithium.

Examples of nitrogen-containing onium salts include ammonium salts optionally substituted with 1 to 4 identical or different groups selected from aryl, alkyl, and aralkyl groups; and nitrogen-containing heterocyclic onium salts optionally substituted with 1 or 2 identical or different groups selected from aryl, alkyl, and aralkyl groups. Preferable examples of nitrogen-containing onium salts include trialkyl ammonium, pyridinium, imidazolium, 1,2,4-triazolium salts, etc.

Other specific examples of compound (1) of the present invention include compounds represented by formula (1), wherein R is a phenyl group optionally substituted with 1 or 2 halogen atoms, and n is 1 or 2 (particularly 2); and tri ($C_1$-$C_6$) alkyl ammonium salts of such compounds.

Furthermore, the present invention provides, as synthetic intermediates of compound (1) or of a salt of compound (1), a compound represented by formula (2):

$$R—S—CF_2—SO_3H \qquad (2)$$

wherein each symbol is as previously defined, or a salt of the compound;

a compound represented by formula (3):

$$R—S(=O)_n—CF_2—SO_2X \qquad (3)$$

wherein X is a halogen atom, and the other symbols are as previously defined, with the proviso that the compound is not $CF_3SO_2CF_2SO_2F$, $FSO_2CF_2SO_2CF_2SO_2F$, or $CF_3SO_2CF_2SO_2CF_2SO_2F$; and a compound represented by formula (4):

$$R—S—CF_2—SO_2X \qquad (4)$$

wherein each symbol is as previously defined.

These compounds are novel compounds. R in compounds (2) to (4) is the same as R in compound (1). The halogen atom shown by X in compounds (3) and (4) is fluorine, chlorine, bromine, or iodine.

In the present invention, compound (1) and salts thereof may be produced by, for example, the following <Scheme 1> and <Scheme 2>. However, the present invention is not limited to these schemes.

<Scheme 1>

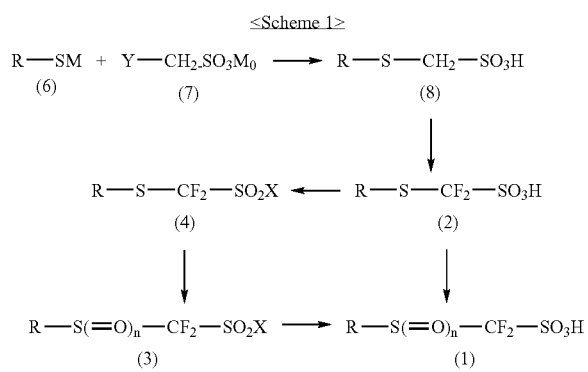

wherein M is a hydrogen atom or a metal atom, Y is a halogen atom, $M_0$ is a metal atom, and the other symbols are as defined previously.

Compound (8) can be produced by reacting compound (6) and compound (7) in the presence of solvent, either in the presence of or in the absence of base, and carrying out acid treatment. Here, any alkali metal, such as Li, Na, or K, may be used as the metal atom represented by $M_0$. Any solvent may be used as long as it does not unfavorably affect the reaction. Examples of solvents include tetrahydrofuran, dioxane, acetonitrile, dimethylsulfoxide, methanol, ethanol, water; mixed solvents thereof; etc. Examples of bases include sodium hydroxide, potassium hydroxide, potassium carbonate, sodium hydride, potassium hydride, etc. When M is a metal atom, the reaction can be conducted without using a base. The equivalent ratio of compound (7) to compound (6) is about 0.1:1 to about 10:1, and preferably about 0.5:1 to about 2:1. The equivalent ratio of base to compound (6) is about 0.5:1 to about 10:1, and preferably about 0.8:1 to about 1.5:1. Reaction temperature is usually about −20° C. to about 200° C. Acids suitable for acid treatment are, for example, hydrochloric acid, sulfuric acid, etc.

Compound (2) can be produced by fluorinating compound (8) with a fluorinating agent in the presence of or in the absence of solvent. Any solvent may be used as long as it does not unfavorably affect the reaction. Examples of solvents include tetrahydrofuran, dioxane, acetonitrile, dimethylsulfoxide, hexane, heptane, octane, methylene chloride, ethyl acetate, formic acid, acetic acid, hydrogen fluoride; mixed solvents thereof; etc. Examples of fluorinating agents include $XeF_2$, acetyl hypofluorite, N-fluoropyridinium salts, N-fluoro-2,4,6-trimethylpyridinium salts, N,N'-difluoro-2,2'-bipyridinium salts, 1-fluoro-4-chloromethyl-1,4-diazoniabicyclo[2.2.2]octane bis(tetrafluoroborate), iodine pentafluoride, fluorine gas, etc. Iodine pentafluoride is especially preferable. The equivalent ratio of fluorinating agent to compound 8 is about 0.8:1 to about 10:1, and preferably about 1:1 to about 5:1. Reaction temperature is usually about −100° C. to about 200° C. Compound (2) can also be obtained, without acid treatment, as a salt formed with the base used in the reaction.

Compound (1) can be produced by oxidizing compound (2) or a salt thereof with an oxidizing agent in the presence of solvent. Any solvent may be used as long as it does not unfavorably affect the reaction. Examples of solvents include acetonitrile, methanol, ethanol, methylene chloride, water, acetic acid; mixed solvents thereof; etc. Examples of oxidizing agents include hydrogen peroxide, peracetic acid, hydroperoxide, potassium peroxysulfate, permanganate, sodium perborate, oxygen/transition metal catalysts, sodium metaperiodate, metachloroperbenzoic acid, osmium (VII) oxide, ruthenium (VII) oxide, nitric acid, chromic acid, sodium dichromate, halogens, sodium hypochlorite, iodobenzene dichloride, iodobenzene diacetate, ozone, singlet oxygen, etc. Compound (1) can be produced by using such oxidizing agents. From the viewpoints of convenience and economic efficiency, the oxidation reaction using hydrogen peroxide is preferable. A method using hydrogen peroxide is disclosed in, for example, Pestycydy, (1-2), 29-41, (2001). Even when compound (2) is a salt, a salt of the intended compound (1) can be obtained in the above-described manner.

Compound (4) can be produced by halogenating compound (2) or a salt thereof (forming a sulfonyl halide) with a halogenating agent. Examples of halogenating agents include thionyl chloride, oxalyl chloride, phosphoryl chloride, phosphorus pentachloride, etc. The reaction may be conducted using known conditions.

Compound (3) can be produced by using compound (4) as a starting material and following the same method as for producing compound (1) from compound (2).

Compound (1) can be produced by hydrolyzing compound (3). Hydrolysis can be carried out under basic conditions or under acidic conditions. Examples of bases include alkali metal bases such as sodium hydroxide, potassium hydroxide, and lithium hydroxide; ammonia; and organic bases such as diethylamine, diisopropylamine, triethylamine, aniline, and pyridine. Examples of acids include hydrochloric acid, sulfuric acid, nitric acid, formic acid, acetic acid, trifluoroacetic acid, methanesulfonic acid, trifluoromethanesulfonic acid, etc. The equivalent ratio of acid or base to compound (4) is usually about 0.5:1 to about 5:1. If necessary, the obtained sulfonic acid may be converted to various salts according to known methods.

<Scheme 2>

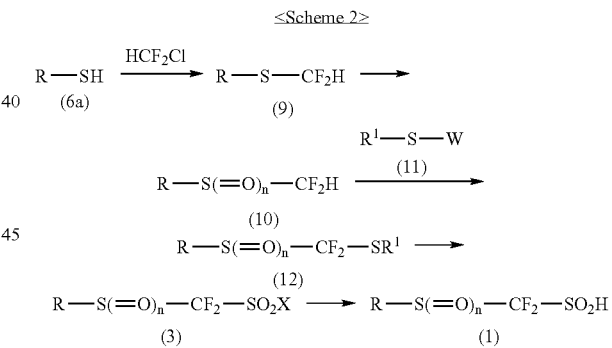

wherein $R^1$ is an optionally substituted alkyl group, an optionally substituted haloalkyl group, an optionally substituted cycloalkyl group, or an optionally substituted aryl group; W is a halogen atom, $-SR^1$, or $-SO_2R^1$; and the other symbols are as defined previously.

The optionally substituted alkyl group, optionally substituted haloalkyl group, optionally substituted cycloalkyl group, and optionally substituted aryl group represented by $R^1$ are the same as those represented by R in compound (1) of the present invention.

Compound (9) can be produced by reacting compound (6a) with a known compound $HCF_2Cl$ in the presence of base in a solvent. Production can be conducted as described in, for example, Pestycydy (1-2), 29-41, (2001).

Compound (10) can be produced by using compound (9) as a starting material and following the same method as for producing compound (1) from compound (2) according to scheme 1. A preferable oxidizing agent is hydrogen peroxide.

Compound (12) can be produced by reacting compound (10) with compound (11) in the presence of base in a solvent. Any solvent may be used as long as it does not unfavorably affect the reaction. Examples of solvents include tetrahydrofuran, dioxane, acetonitrile, dimethylsulfoxide, dimethylformamide, methylene chloride, water, etc. Examples of bases include sodium hydroxide, potassium hydroxide, potassium tert-butoxide, sodium hydride, potassium hydride, etc. The equivalent ratio of compound (11) to compound (10) is usually about 0.5:1 to about 5:1, and preferably about 1:1 to about 2:1. The equivalent ratio of base to compound (10) is about 0.5:1 to about 5:1, and preferably about 0.8:1 to about 1.2:1. Reaction temperature is usually about $-100°$ C. to about $100°$ C. Production can be conducted as described in, for example, J. Fluorine. Chem., 43, 53-66, (1989).

Compound (3) can be produced by oxidizing compound (12) with an oxidizing agent. Examples of oxidizing agents include molecular halogens, particularly chlorine (gas) (oxidative chlorination reaction). Production can be conducted as described in, for example, J. Org. Chem., 44, 1708-1711, (1979); J. Fluorine. Chem., 43, 27-34, (1989); U.S. Pat. No. 4,329,435; etc.

To facilitate oxidation, $R_1$ is preferably a benzyl group, linear $C_1$ to $C_6$ alkyl group, t-butyl group, etc. Among these, the benzyl group is especially preferable.

When X is a fluorine atom (F), fluorine gas may be used, but synthesis can also be carried out by further reacting a sulfonyl chloride with a fluoride such as potassium fluoride.

Compound (1) can be produced by using compound (3) as a starting material and following the same method as for producing compound (1) from compound (3) according to scheme 1.

In synthesizing the intended compound of the present invention, functional groups may be protected by suitable protective groups, and if protection is no longer necessary, deprotection may be carried out. The use of protective groups can be suitably determined based on the knowledge of those skilled in the art.

In the present invention, unless otherwise indicated, "alkyl" indicates linear or branched $C_1$ to $C_{20}$ alkyl, and preferably linear or branched $C_1$ to $C_6$ alkyl. "Haloalkyl" indicates linear or branched $C_1$ to $C_{20}$ haloalkyl, and preferably linear or branched $C_1$ to $C_6$ haloalkyl. In a haloalkyl, at least one hydrogen atom in a linear or branched $C_1$ to $C_{20}$ alkyl is substituted by halogen atom. "Alkenyl" indicates linear or branched $C_2$ to $C_{20}$ alkenyl, and preferably linear or branched $C_2$ to $C_6$ alkenyl. "Alkynyl" indicates linear or branched $C_2$ to $C_{20}$ alkynyl, and preferably linear or branched $C_2$ to $C_6$ alkynyl. "Cycloalkyl" indicates linear or branched $C_3$ to $C_{10}$ cycloalkyl, and preferably linear or branched $C_3$ to $C_7$ cycloalkyl. "Alkoxy" indicates linear or branched $C_1$ to $C_{20}$ alkoxy, and preferably linear or branched $C_1$ to $C_6$ alkoxy. "Aryl" indicates monocyclic, bicyclic, or tricyclic $C_6$ to $C_{14}$ aryl, and preferably phenyl. "Aralkyl" indicates $C_1$ to $C_{15}$ aralkyl, and preferably $C_1$ to $C_8$ aralkyl. "Halogen atom" indicates fluorine, chlorine, bromine, or iodine atom. Examples of "acyl" include linear and branched $C_1$ to $C_6$ alkanoyl groups such as formyl, acetyl, propionyl, n-butyryl, isobutyryl, valeryl, isovaleryl, and pivaloyl; arylcarbonyl groups such as benzoyl and naphthoyl; etc. Examples of "carbamoyl" are represented by the formula: $-\text{CONR}^c\text{R}^d$. $R^c$ and $R^d$ each independently represent, for example, a hydrogen atom, and alkyl, haloalkyl, aryl, haloaryl, aralkyl groups, etc. Examples of these groups are as mentioned above.

II. Characteristics of the Compounds of the Present Invention

The fluorosulfonic acids of the present invention are novel compounds which have never been reported before, and possess the feature of having high acidity. Generally, when there is a substituent near the sulfonic acid group, the greater the electron-withdrawing capability of this substituent, the easier is dissociation of the sulfonic acid proton, thus providing high acidity. In the fluorosulfonic acids of the present invention, the $-CF_2-SO_3H$ group is linked to $R-S(=O)_n-$, which is a group having an extremely high electron-withdrawing property; therefore, they show high acidity.

For reference, the Hammett constants of various substituents are shown below (*Kagaku Binran* (Handbook of Chemistry), edited by the Chemical Society of Japan, basic vol., 4th ed., II, 347-348).

| Substituent | $\sigma_m$ | $\sigma_p$ |
|---|---|---|
| $C_6H_5$ | 0.04 | 0.02 |
| F | 0.34 | 0.06 |
| $CONH_2$ | 0.28 | 0.31 |
| $CO_2R$ | 0.35 | 0.44 |
| $COCH_3$ | 0.36 | 0.47 |
| $CF_3$ | 0.46 | 0.53 |
| $SOCH_3$ | 0.52 | 0.49 |
| $SO_2NH_2$ | 0.53 | 0.58 |
| $SF_5$ | 0.61 | 0.68 |
| CN | 0.62 | 0.71 |
| $SO_2CH_3$ | 0.68 | 0.73 |
| $SO_2CF_3$ | 0.76 | 0.96 |

As shown in the above table, the Hammett constants of the $-SOCH_3$, $-SO_2CH_3$, and $-SO_2CF_3$ substituents are high. In particular, the Hammett constants of $SO_2CH_3$ and $SO_2CF_3$ are extremely high. Since the fluorosulfonic acids of the present invention contain these groups, they show high acidity.

In addition, the fluorosulfonic acids of the present invention are advantageous in that various functional groups can be easily introduced into the group R, as is clear from the above description of the process for producing the compounds of the present invention.

III. Uses of the Compounds of the Present Invention

As described above, the fluorosulfonic acids of the present invention have high acidity. Therefore, the fluorosulfonic acids and salts thereof can be used as catalysts (acid catalysts) in synthetic reactions.

The compounds of the present invention can be used as photo acid generators for resist materials, the photo acid generators being suitable for use in resists (chemical amplification photoresists, liquid crystal color filters, etc.) because they efficiently generate acid when they are irradiated with light.

The fluorosulfonic acid salts of the present invention can be used as electrolytes for various cells. They are suitable as, for example, electrolytes for lithium ion (primary or secondary) cells, and especially as electrolytes for nonaqueous lithium ion (primary or secondary) cells. Examples of solvents for electrolytes include known nonaqueous organic solvents such as propylene carbonate, ethylene carbonate, diethyl carbonate, dimethyl carbonate, methyl ethyl carbonate, dimethoxyethane, γ-butyrolactone, methyl acetate, methyl formate, etc. An electrolytic solution can be obtained by providing such a solvent with a compound of the present invention as part of the electrolyte. Naturally, it is preferable to use an electrolytic solution having a water content of not more than 10 ppm.

As mentioned in, for example, J. Electrochem. Soc., (2000), 147, 34, salts of the fluorosulfonic acids of the present invention can be used as electrolytes for nonaqueous solutions having lithium ion conductivity, and as gel electrolytes wherein the electrolyte is fixed by a polymer matrix. Known materials may be used for the positive electrode, negative electrode, separator, etc., of a lithium ion (primary or secondary) cell. Cells may be, for example, cylindrical, rectangular, coin-shaped, film-shaped, etc. Examples of negative electrode materials include lithium metal and lithium alloys; carbon materials and polymeric materials capable of doping/dedoping lithium; lithium-intercalation compounds such as metal oxides; etc. Examples of positive electrode materials include mixed oxides of lithium and transition metal(s), such as $LiCoO_2$, $LiNiO_2$, $LiMn_2O_4$, and $LiMnO_2$; polymeric materials; etc. Separators may be formed of, for example, porous membranes of polymeric materials such as polyethylene and polypropylene; polymeric materials (so-called gel electrolytes) that occlude and fix the electrolytic solution of the present invention; etc. Examples of collector materials include copper, aluminum, stainless steel, titanium, nickel, tungsten steel, carbon materials, etc. A collector may be in the shape of, for example, a foil, net, nonwoven fabric, punched metal, etc.

Furthermore, the salts of the fluorosulfonic acids of the present invention can be used for photosensitized solar cell electrolytic solutions, capacitor electrolytes or electrolytic solutions, or for electrochromism, photochromism, etc.

BEST MODE FOR CARRYING OUT THE INVENTION

Hereinafter, the present invention is described in further detail with reference to examples. However, the invention is not limited to these examples.

Example 1

Synthesis of triethylammonium (4-chlorophenylthio)difluoromethanesulfonate

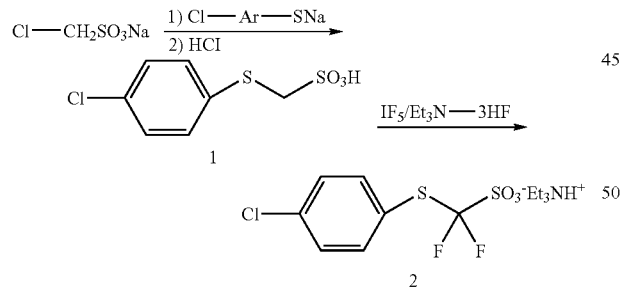

A solution of sodium hydroxide (7.98 g, 0.20 mol) in water (150 ml) was added to a solution of p-chlorobenzenethiol (26.0 g, 0.18 mol) in methanol (150 ml) with stirring under ice-cooling, and then further stirred at room temperature for 30 minutes (reaction mixture A). Sodium chloromethanesulfonate (22.9 g, 0.15 mol) was placed in a 500 liter stainless autoclave, and reaction mixture A prepared above was added thereto. The temperature was gradually raised from room temperature to 160° C., and the resulting mixture was stirred at 160° C. for 17 hours. The reaction mixture was concentrated under reduced pressure, and ethyl acetate was added to the obtained residue. The crystals that did not dissolve in the ethyl acetate were collected by filtration, thoroughly washed with ethyl acetate, and dried, giving crude crystals (about 40 g). These crude crystals were extracted using ethanol by a Soxhlet extractor and purified, thus giving (4-chlorophenylthio)methanesulfonic acid 1 (21.9 g, yield: 56%).

Under an argon atmosphere, $Et_3N \cdot 3HF$ (38.7 g, 240 mmol) and $IF_5$ (53.3 g, 240 mmol) were placed in a reaction vessel made of fluororesin, and then stirred. Heptane (160 ml) was added thereto, and under ice-cooling, (4-chlorophenylthio)methanesulfonic acid 1 (20.9 g) was added over about 1 minute. The ice bath was removed, and the temperature was gradually raised from room temperature. The mixture was stirred at 70° C. for 16 hours and allowed to cool. The reaction mixture was then added to water (800 ml), and extracted 3 times using dichloromethane. To the extracted organic layer was added fluorobenzene (1.88 ml, 20 mmol) as an internal standard. $^{19}F$-NMR spectrum measurement was conducted to find that triethylammonium (4-chlorophenylthio)difluoromethanesulfonate 2 was generated in a yield of about 59%. The organic layer was washed twice with an aqueous sodium thiosulfate solution and once with water, and then dried with anhydrous magnesium sulfate. After the drying agent was removed by filtration, the solution was concentrated, giving crude crystals (15.3 g). These crude crystals were recrystallized from ethyl acetate/n-hexane, giving triethylammonium (4-chlorophenylthio)difluoromethanesulfonate 2 (9.7 g, yield: 32%).

2: $^{1}H$-NMR(500 MHz, $CDCl_3$) (ppm): 1.38(9H, t, J=7.4 Hz), 3.16(6H, qd, J=7.4, 4.9 Hz), 7.35(2H, dm, J=8.6 Hz), 7.63(2H, dm, J=8.6 Hz).

$^{19}F$-NMR(500 MHz, $CDCl_3$)(ppm): −79.1(2F, s).

Example 2

Synthesis of triethylammonium (4-chlorophenylsulfonyl)difluoromethanesulfonate

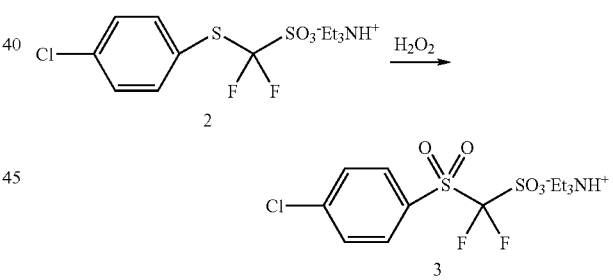

An acetic acid (1 ml) solution of 31% hydrogen peroxide solution (643 mg, 5.9 mmol) was added dropwise to an acetic acid (1 ml) solution of triethylammonium (4-chlorophenylthio)difluoromethanesulfonate 2 (220 mg, 0.59 mmol) at room temperature. The temperature of the mixed solution was gradually raised to 80° C., and heating was continued for 3 days. An acetic acid (1 ml) solution of 31% hydrogen peroxide solution (643 mg, 5.9 mmol) was further added to the reaction system, and heating was continued at 100° C. for 3 days. After the reaction solution was allowed to cool, fluorobenzene (94 μl, 1 mmol) was added to the system as an internal standard. $^{19}F$-NMR spectrum measurement was conducted to find that triethylammonium (4-chlorophenylsulfonyl)difluoromethanesulfonate 3 (yield: 77%) and triethylammonium (4-chlorophenylsulfinyl)difluoromethanesulfonate 4 (yield: 6%) were generated. The reaction solution was neutralized with triethylamine and extracted using dichloromethane. The organic layer was washed with water, and was dried with anhydrous magnesium sulfate. After the drying agent was removed by filtration, the solution was concentrated, giving crude crystals (206 mg). These crude crystals were purified on a silica gel plate using methanol as an eluent, thus giving triethylammonium (4-chlorophenylsulfonyl)difluoromethanesulfonate 3 (117 mg, yield: 49%).

3: $^1$H-NMR(500 MHz, CD$_3$OD) (ppm): 1.29(9H, t, J=7.3 Hz), 3.15(6H, q, J=7.3 Hz), 7.68(2H, dm, J=8.8 Hz), 8.01(2H, dm, J=8.8 Hz).

$^{19}$F-NMR(500 MHz, CD$_3$OD) (ppm): −103.6(2F, s).

Example 3

Synthesis of triethylammonium (4-chlorophenylsulfonyl)difluoromethanesulfonate

A suspension of Oxone (2 KHSO$_5$·KHSO$_4$·K$_2$SO$_4$) (197 mg) in water (0.75 ml) was added to a solution of triethylammonium (4-chlorophenylthio)difluoromethanesulfonate 2 (72 mg, 0.16 mmol) in methanol (1 ml), and stirred at room temperature for 1 day. Methanol (0.5 ml), water (0.38 ml), and Oxone (100 mg) were then added to the reaction mixture, and stirred for 7 days. $^{19}$F-NMR spectrum measurement of the reaction solution was conducted to find that triethylammonium (4-chlorophenylsulfonyl)difluoromethanesulfonate 3 and triethylammonium (4-chlorophenylsulfinyl)difluoromethanesulfonate 4 were generated in a ratio of 82:18.

Example 4

Synthesis of triethylammonium (4-chlorophenylsulfinyl)difluoromethanesulfonate

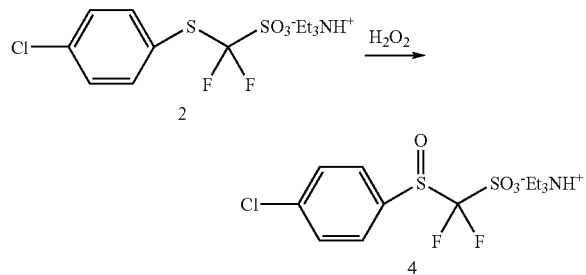

An acetic acid (1 ml) solution of 31% hydrogen peroxide solution (292 mg, 2.66 mmol) was added dropwise to an acetic acid (2.5 ml) solution of triethylammonium (4-chlorophenylthio)difluoromethanesulfonate 2 (500 mg, 1.33 mmol) at room temperature. The temperature of the mixed solution was gradually raised to 80° C., and heating was continued for 20 hours. After the reaction solution was allowed to cool, fluorobenzene (188 μl, 2 mmol) was added to the reaction system as an internal standard. $^{19}$F-NMR spectrum measurement was conducted to find that triethylammonium (4-chlorophenylsulfinyl)difluoromethanesulfonate 4 (yield: 77%) and triethylammonium (4-chlorophenylsulfonyl)difluoromethanesulfonate 3 (yield: 23%) were generated. The reaction solution was neutralized with triethylamine and extracted using dichloromethane. The organic layer was washed with water, and was dried with anhydrous magnesium sulfate. After the drying agent was removed by filtration, the solution was concentrated, giving an oily substance (334 mg). This oily substance was further purified on a silica gel plate using methanol as an eluent.

4: $^1$H-NMR(500 MHz, CD$_3$OD) (ppm):1.28(9H, t, J=7.3 Hz), 3.13(6H, q, J=7.3 Hz), 7.62(2H, dm, J=8.7 Hz), 7.82(2H, dm, J=8.7 Hz).

$^{19}$F-NMR(500 MHz, CD$_3$OD) (ppm): −104.8(1F, d, J=204 Hz), −108.7(1F, d, J=204 Hz).

Example 5

Synthesis of Sulfide Compound 6

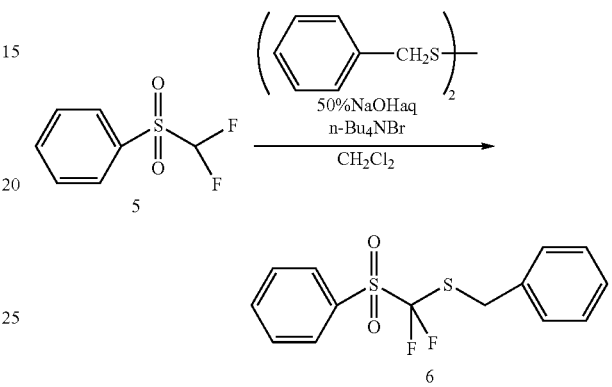

Benzyl disulfide (638 mg, 2.59 mmol) and tetrabutylammonium bromide (20 mg) were added to a solution of difluoromethanesulfonylbenzene 5 (500 mg, 2.59 mmol) in dichloromethane (6 ml). A 50% aqueous solution of sodium hydroxide (6 ml) was added dropwise thereto at room temperature, and the resulting mixture was stirred at room temperature for 24 hours. While being cooled, water and ethyl acetate were added to the mixture, and ethyl acetate extraction was performed twice. The extract was washed with dilute hydrochloric acid and brine, and was dried with anhydrous magnesium sulfate. After the drying agent was removed by filtration, the solution was concentrated. The obtained residue was purified by silica gel column chromatography (hexane: ethyl acetate=10:1), giving sulfide compound 6 (yield: 66%) as colorless crystals.

6: $^1$H-NMR(500 MHz, CDCl$_3$) (ppm): 4.32(2H, s), 7.28-7.35 (5H, m), 7.55-8.05(5H, m,)

$^{19}$F-NMR(500 MHz, CDCl$_3$) (ppm): −81.0(s)

HRMS: theoretical value 314.02468 (M$^+$) measured value 314.02422 (M$^+$)

Melting point: 54.1° C.-55.2° C.

Example 6

Synthesis of Sulfonyl Compound 7

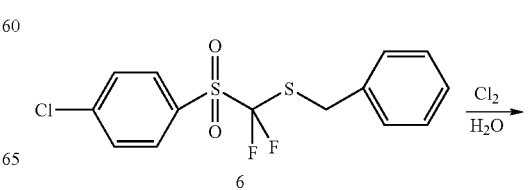

-continued

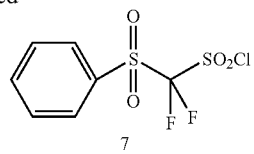

Sulfide compound 6 (1 g, 3.19 mmol) was dispersed in water (10 ml), and chlorine gas was bubbled thereinto at an internal temperature of 0° C. to 5° C. for 4 hours. While being cooled, water and dichloromethane were added thereto, and dichloromethane extraction was performed twice. The extract was washed with brine, and was dried with anhydrous magnesium sulfate. After the drying agent was removed by filtration, the solution was concentrated, giving an oily substance (970 mg). Fluorobenzene (299 μl, 3.19 mmol) was added to the reaction system as an internal standard. $^{19}$F-NMR spectrum measurement was conducted to find that sulfonyl chloride 7 was generated in a yield of 91%, the yield being calculated on the basis of the internal standard.

7: $^1$H-NMR(500 MHz, CDCl$_3$) (ppm): 7.72-8.15(5H, m)
$^{19}$F-NMR(500 MHz, CDCl$_3$) (ppm): −96.0(s)

Example 7

Synthesis of Sulfide Compound 8

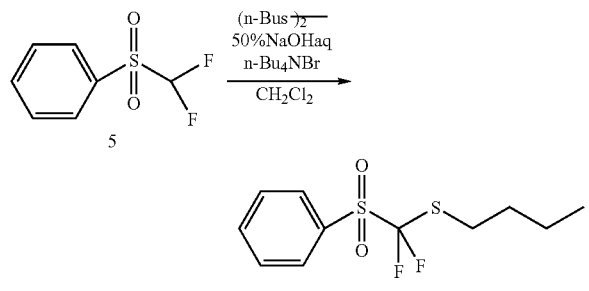

Tetrabutylammonium bromide (20 mg) and n-butyl disulfide (492.5 μl, 2.59 mmol) were added to a solution of difluoromethanesulfonylbenzene 5 (500 mg, 2.59 mmol) in dichloromethane (6 ml). A 50% aqueous solution of sodium hydroxide (6 ml) was added dropwise thereto at room temperature, and the resulting mixture was stirred at room temperature for 72 hours. While being cooled, water and ethyl acetate were added to the mixture, and ethyl acetate extraction was performed twice. The extract was washed with dilute hydrochloric acid and brine, and was dried with anhydrous magnesium sulfate. After the drying agent was removed by filtration, the solution was concentrated. The obtained residue was purified by silica gel column chromatography (hexane: ethyl acetate=10:1), giving sulfide compound 8 (yield: 67%) as transparent colorless liquid.

8: $^1$H-NMR(500 MHz, CDCl$_3$) (ppm): 0.93(3H, t, J=7.34), 1.45(2H, dt, J=7.34, 7.25), 1.67(2H, dd, J=7.25, 7.46), 3.08 (2H, t, J=7.46), 7.54-8.05(5H,m)
$^{19}$F-NMR(500 MHz, CDCl$_3$) (ppm): −80.6(s)

Example 8

Synthesis of Sulfonyl Compound 7

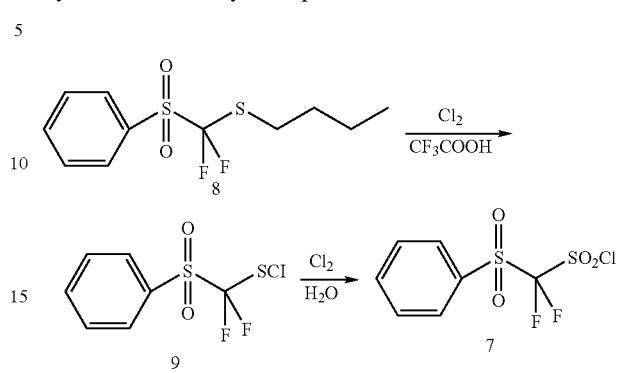

(1) Sulfide compound 8 (1 g, 3.56 mmol) was dissolved in trifluoroacetic acid (10 ml), and chlorine gas was bubbled thereinto at an internal temperature of 0° C. to 5° C. for 10 hours. Fluorobenzene (334 μl, 3.56 mmol) was added to the reaction system as an internal standard. $^{19}$F-NMR spectrum measurement was conducted to find that sulfur chloride compound 9 (yield: 55%) was generated. The solution was concentrated, giving an oily substance (820 mg).

9: $^1$H-NMR(500 MHz, CDCl$_3$) (ppm): 7.63-8.10(5H, m)
$^{19}$F-NMR(500 MHz, CDCl$_3$) (ppm): −81.1(s)

(2) The unpurified sulfur chloride compound 9 (820 mg) was dispersed in water (10 ml), and chlorine gas was bubbled thereinto at an internal temperature of 0° C. to 5° C. for 5 hours. While being cooled, water and dichloromethane were added to the mixture, and dichloromethane extraction was performed twice. The extract was washed with brine and dried with anhydrous magnesium sulfate. After the drying agent was removed by filtration, the solution was concentrated, giving an oily substance (450 mg). Fluorobenzene (334 μl, 3.56 mmol) was added to the reaction system as an internal standard. $^{19}$F-NMR spectrum measurement was conducted to find that sulfonyl compound 7 was generated in a total yield of 45% from sulfide compound 8.

The sulfonyl compound thus obtained can be converted to the sulfonic acid (or a salt thereof) by known methods.

7: $^1$H-NMR(500 MHz, CDCl$_3$) (ppm): 7.72-8.15(5H, m)
$^{19}$F-NMR(500 MHz, CDCl$_3$) (ppm): −96.0(s)

The disclosures of the documents cited in this specification are incorporated herein by reference.

EFFECT OF THE INVENTION

The fluorosulfonic acids of the present invention have greater stability and higher acidity than conventional fluorosulfonic acids. Various derivatives can be easily synthesized by the processes for producing fluorosulfonic acid compounds according to the present invention. The fluorosulfonic acid compounds of the present invention are suitable for an extensive range of uses such as strong acid catalysts, electrolytes, etc.

The invention claimed is:

1. A compound represented by formula (1):

$$R-S(=O)_n-CF_2-SO_3H \qquad (1)$$

wherein R is an optionally substituted alkyl group, an optionally substituted haloalkyl group, an optionally substituted alkenyl group, an optionally substituted haloalkenyl group, an optionally substituted alkynyl group, an optionally substituted haloalkynyl group, an optionally substituted cycloalkyl group, an optionally substituted cycloalkenyl group, an optionally substituted aryl group, an optionally substituted heterocyclic group, an optionally substituted alkoxycarbonyl group, an optionally substituted alkenyloxycarbonyl group, an optionally substituted alkynyloxycarbonyl group, an optionally substituted aryloxycarbonyl group, an optionally substituted acyl group, an optionally substituted carbamoyl group, or a cyano group; and n is 1 or 2;

or a salt of the compound.

2. An electrolyte comprising the compound or salt thereof according to claim 1.

3. An acid catalyst comprising the compound or salt thereof according to claim 1.

4. A cell comprising the electrolyte of claim 2.

5. A compound or salt thereof according to claim 1, wherein R is an optionally substituted haloalkyl group.

6. A compound or salt thereof according to claim 1, wherein R is an optionally substituted aryl group.

* * * * *